United States Patent [19]

Wood

[11] Patent Number: Plant 6,700

[45] Date of Patent: Mar. 28, 1989

[54] BLUEBERRY-VARIETY REKA

[75] Inventor: Franklin H. Wood, Hamilton, New Zealand

[73] Assignee: Maftech North, Ruakura Agricultural Research Centre, Hamilton, New Zealand

[21] Appl. No.: 102,151

[22] Filed: Sep. 28, 1987

[30] Foreign Application Priority Data

Sep. 29, 1986 [NZ] New Zealand ..... PV 3/50/2

[51] Int. Cl.[4] ..... A01H 5/03

[52] U.S. Cl. ..... Plt./33

[58] Field of Search ..... Plt./33

*Primary Examiner*—Robert E. Bagwill

*Attorney, Agent, or Firm*—Abelman Frayne Rezac & Schwab

[57] ABSTRACT

A blueberry plant which bears high yields of medium-large berries early in the season.

4 Drawing Sheets

In 1969, seed from a range of blueberry crosses was gifted to Ruakura as a result of an agreement between P. Bates (Ruakura) and A.D. Draper (USDA). The NZ objective was to identify plant material which was more suitable for local conditions. Over a thousand seedlings were initially screened in the first stage evaluation from which forty seedling types were identified as promising. Closer critical examination of these seedlings over several years, resulted in the selection of ten elite types. Seven of these ten seedlings had Earliblue, Blue-crop parentage and characteristically produced early maturing, high quality fruit. The remainder had Berkeley and Blueray parentage and typically produced later maturing fruit. These elite seedlings were planted out in 1982 in a fully replicated trial to determine their commerical usefulness, Puru, Nui and Reka, three elite Ruakura selections, are change seedlings arising from Earliblue and Bluecrop crosses. They are the product of careful screening and evaluation which has taken place over many years.

COMPARISON OF REKA AND SIMILAR CULTIVARS

Reka, also a seedling with Earliblue, Bluecrop parentage is probably the most outstanding selection of the three new cultivars. A consistently high yielding, early cropper, Reka is easily distinguishable from standard selections as well as from Puru and Nui. Fruit size is on average smaller than that of Puru and Nui (see Table 2), however other berry qualities such as scar size and shelf life compare favourably. As with Puru and Nui, the five standard cultivars that best compare with Reka are Earliblue, Collins, Stanley, Darrow and Bluecrop. Table 1 summarizes basic similarities and differences and the precise nature of these are included in attached tables and figures.

Physical differences such as the predominance of pubescence on stems and beneath leaves as well as the characteristic colour of mature stems and fruit enables fairly rapid field identification.

The drawings show flowers, fruit, bush habit, and fruit production data.

DETAILED DESCRIPTION OF REKA

Figure 1:
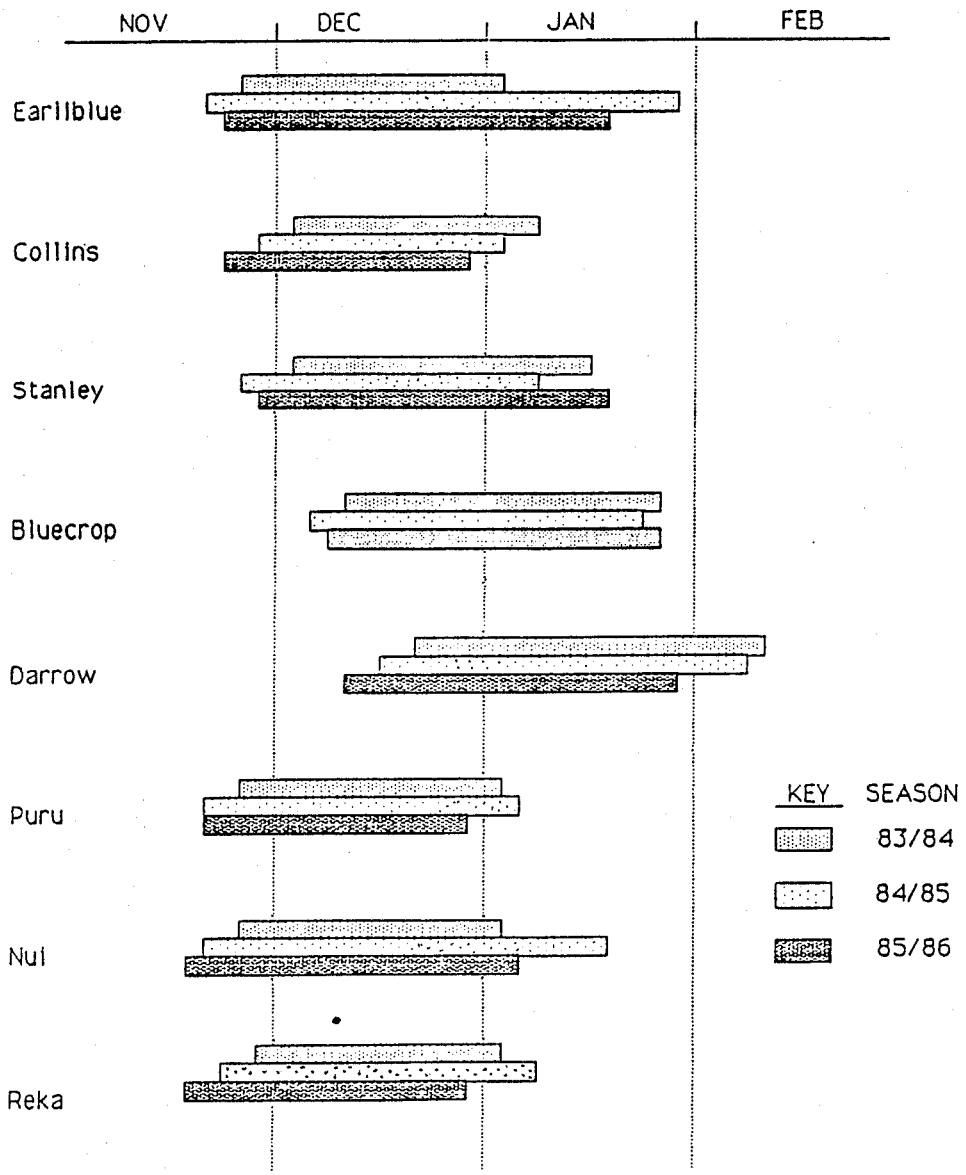
Figure 2:
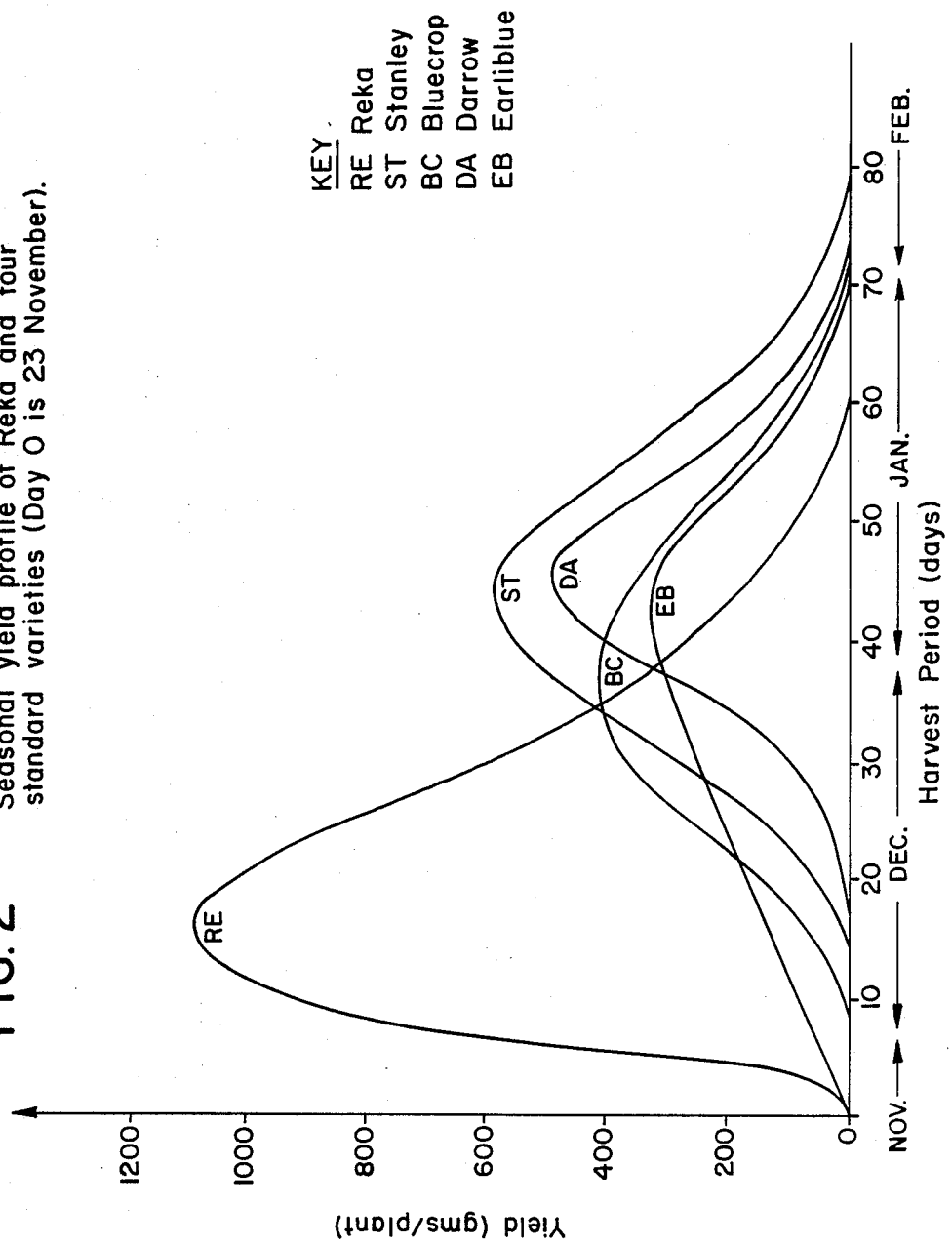

Seedling reference: No. 17.

Flowering habit: White flower with a delicate pink blush and faint pink stripe. Elongated flower (cylindraceous). Flowering takes place in the first or second week of September, which is early to mid season in the Southern Hemisphere.

Cluster: Large clusters of 8–12 flowers.

Leaves: Deciduous shiny green leaves, average length 63 mm and average width 36 mm with slightly indented veins. Predominantly ovate with pubescence undersides.

Stems: Slightly pubescence stems which are green/pink when young and turn pink/red with age.

Fruit: Moderate to large greyish blue fruit, average-diameter being 14 mm and average weight being 1.6 g. Small dry scar. Fruit matures from mid to late November to early January which is early in the fruiting season in the Southern Hemisphere. The clusters are relatively tight, have medium aroma, average tendency of the fruit to drop when ripe and low resistance to cracking.

TABLE 1

Similarities and differences between Reka and five standard cultivars.

| Cultivar | Similarities | Differences* |
|---|---|---|
| Earliblue | flavour | berry colour |
| | berry size | less bush vigour |
| | early maturing habit | less precocious |
| | | larger scar |
| | | extended harvest |
| | | spreading growth habit |
| Collins | early maturing habit | less precocious |
| | flavour | less bush vigour |
| | berry size | larger scar |
| Stanley | early maturing habit | less precocious |
| | bush vigour | smaller berry size |
| | berry colour | larger scar |
| Darrow | bush vigour | larger berry size |
| | berry colour | less precocious |
| | | later maturing |
| | | larger scar |
| | | berry flavour |
| Bluecrop | bush vigour | less precocious |
| | flavour | later maturing |
| | scar | berry colour |
| | berry size | |

(*cultivar differences with respect to Reka)

TABLE 2

Fruit production of three new early Ruckura blueberry selections, Puru, Nui and Reka, and five standard varieties.

| | Yield per season (kg/bush) | | | |
|---|---|---|---|---|
| Cultivar | 1 | 2 | 3 | Year 5 onwards (mean) |
| Earliblue | 0.2 | 0.8 | 1.2 | 2,4 |

TABLE 2-continued

Fruit production of three new early Ruckura blueberry selections, Puru, Nui and Reka, and five standard varieties.

| Cultivar | Yield per season (kg/bush) 1 | 2 | 3 | Year 5 onwards (mean) |
|---|---|---|---|---|
| Collins | 0.2 | 0.9 | 1.1 | 1.6 |
| Stanley | 0.3 | 1.1 | 1.9 | 3.1 |
| Bluecrop | 0.1 | 0.5 | 1.4 | 5.8 |
| Darrow | 0.1 | 0.7 | 1.1 | 4.9 |
| Puru | 0.5 | 0.6 | 2.0 | 4.8 |
| Nui | 0.6 | 0.8 | 1.8 | 5.6 |
| Reka | 2.2 | 2.3 | 4.4 | 9.3 |

TABLE 3

Average berry weights of three new early Ruckura selections, Puru, Nui, Reka and five standard varieties.

| Cultivar | Average berry weight (gms) |
|---|---|
| Earliblue | 1.6 |
| Collins | 1.6 |
| Stanley | 1.2 |
| Bluecrop | 1.7 |
| Darrow | 2.0 |
| Puru | 2.2 |
| Nui | 2.1 |
| Reka | 1.6 |

TABLE 4

Pre-Christmas fruit production of three new early varieties, Puru, Nui, Reka and five standard varieties.

| Cultivar | Yield pre-Christmas as a percentage of total production |
|---|---|
| Earliblue | 69 |
| Collins | 82 |
| Stanley | 67 |
| Bluecrop | 55 |
| Darrow | 28 |
| Puru | 91 |
| Nui | 88 |
| Reka | 95 |

TABLE 5

General characteristics of three new early Ruakura selections, Puru, Nui, Reka and five standard varieties.

| Cultivar | Season | Bush Growth Habit | Fruit Size | Fruit Colour | Scar |
|---|---|---|---|---|---|
| Earliblue | v. early | moderate spreading | medium-large | light blue | medium/dry |
| Collins | early | moderate spreading | medium | pale blue | medium/dry |
| Stanley | early | vigorous upright | medium-small | pale blue | medium/dry |
| Bluecrop | mid | vigorous upright | medium-large | pale blue | small/dry |
| Darrow | late | vigorous upright | large | pale blue | medium/wet |
| Nui | v. early | vigorous upright | V. large | pale blue | small/dry |
| Puru | v. early | vigorous upright | large | pale blue | small/dry |
| Reka | v. early | vigorous spreading | medium-large | light blue | small/dry |

Additional Notes (i) Leaf measurements were taken on mature leaves and not at the time of full flowering as the leaves at this stage are still expanding.

(ii) Pubescence on lower leaf surface is confined to central leaf vein only.

(iii) Fruit diameter and weight vary within the season. Early season fruit which is produced on primary whips is larger and heavier than subsequent fruit produced on secondary and tertiary whips.

I claim:

1. A new and distinct variety of blueberry, substantially as herein shown and described, characterised particularly by (a) a high percentage of total yield is produced early in the season, (b) medium-large fruit weight, (c) small dry scar tissue.

* * * * *

FIG. 1 Fruit production season of three new early cultivars Puru, Nui and Reka and five standard varieties.

Seasonal yield profile of Reka and four standard varieties (Day 0 is 23 November).

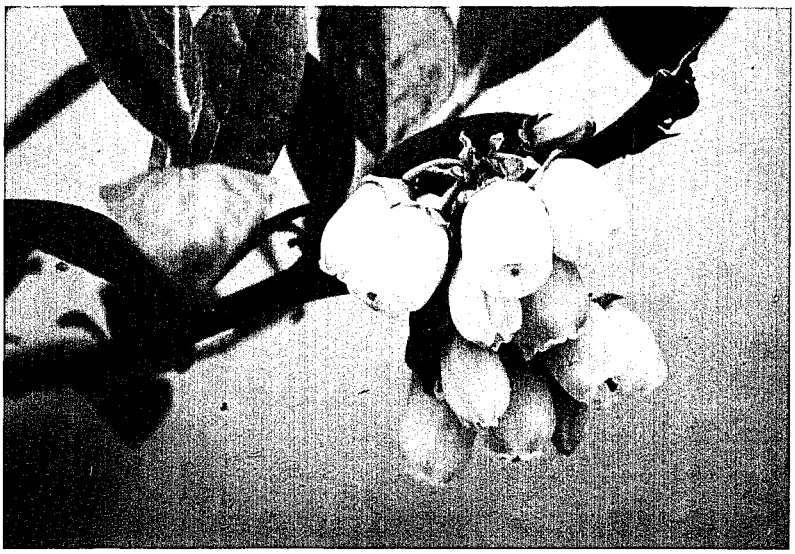
REKA-Floral Development
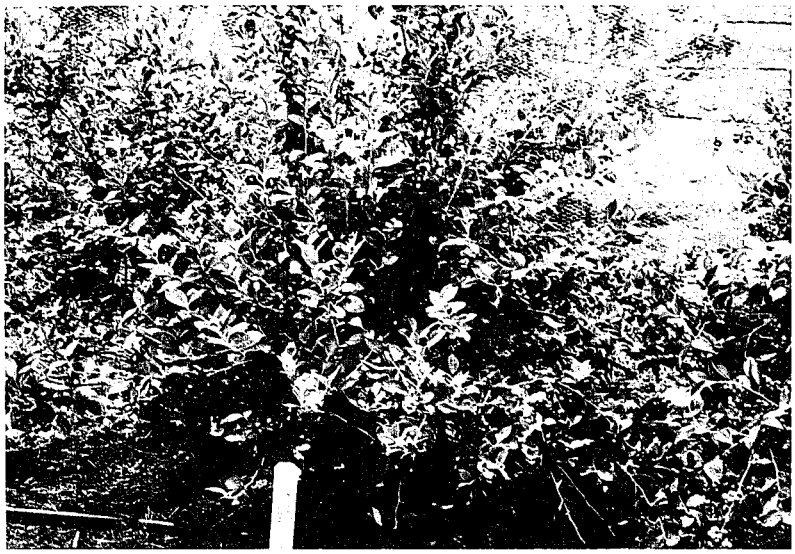
REKA-Bush Habit

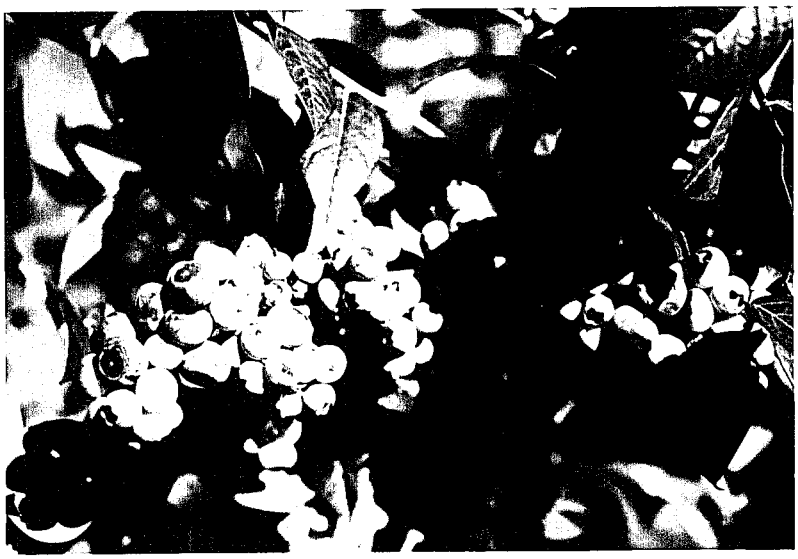
REKA-Fruit Development